(12) United States Patent
Kimura et al.

(10) Patent No.: US 9,551,661 B2
(45) Date of Patent: Jan. 24, 2017

(54) ASSAY CHIP

(71) Applicant: FUJIFILM Corporation, Tokyo (JP)

(72) Inventors: Toshihito Kimura, Ashigarakami-gun (JP); Akihiro Komatsu, Ashigarakami-gun (JP); Toshihiro Mori, Ashigarakami-gun (JP); Hideyuki Karaki, Ashigarakami-gun (JP); Nobuhiko Fujiwara, Ashigarakami-gun (JP); Kouta Katou, Ashigarakami-gun (JP); Tadahiro Matsuno, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 163 days.

(21) Appl. No.: 13/911,872

(22) Filed: Jun. 6, 2013

(65) Prior Publication Data

US 2013/0266480 A1    Oct. 10, 2013

Related U.S. Application Data

(63) Continuation of application No. PCT/JP2011/006933, filed on Dec. 12, 2011.

(30) Foreign Application Priority Data

Dec. 10, 2010    (JP) ................................ 2010-276376

(51) Int. Cl.
    *G01N 33/00*    (2006.01)
    *G01N 21/64*    (2006.01)
    (Continued)

(52) U.S. Cl.
    CPC ......... *G01N 21/6428* (2013.01); *B01L 3/5027* (2013.01); *G01N 21/03* (2013.01);
    (Continued)

(58) Field of Classification Search
    CPC ... G01N 21/6428; G01N 21/03; B01L 3/5027; B01L 2200/025
    See application file for complete search history.

(56) References Cited

U.S. PATENT DOCUMENTS

| 5,147,607 A | 9/1992 | Mochida |
| 5,923,031 A | 7/1999 | Naya |

(Continued)

FOREIGN PATENT DOCUMENTS

| JP | 3-223674 A | 10/1991 |
| JP | 4-225145 A | 8/1992 |

(Continued)

OTHER PUBLICATIONS

International Search Report issued in PCT/JP2011/006933, dated Jan. 17, 2012.

(Continued)

*Primary Examiner* — Sam P Siefke
(74) *Attorney, Agent, or Firm* — Birch, Stewart, Kolasch & Birch, LLP

(57) ABSTRACT

An assay chip includes fluidic-channel member composed of a light-transmissive lower member and an upper member, forming a fluidic-channel therebetween, and a cover member fitted with the fluidic-channel member from the upper-member-side thereof. An inlet for injecting a sample solution into the fluidic-channel and a suction opening for sucking, from the downstream side, the injected sample solution, both communicating with the fluidic-channel, are formed on the upper surface of the upper member. A pot for carrying out predetermined pre-processing on the sample solution, a pot for first-reaction processing to bind a photoresponsive labeling substance to an analyte in the sample solution, an inlet insertion-hole for inserting the inlet, and a suction-opening (Continued)

insertion-hole for inserting the suction opening are linearly arranged on the upper surface of the cover member.

18 Claims, 8 Drawing Sheets

(51) Int. Cl.
   *B01L 3/00* (2006.01)
   *G01N 21/03* (2006.01)
   *G01N 33/543* (2006.01)
(52) U.S. Cl.
   CPC ....... *G01N 21/648* (2013.01); *G01N 21/6408* (2013.01); *G01N 33/54366* (2013.01); *B01L 2200/025* (2013.01); *B01L 2400/0487* (2013.01); *G01N 2021/0328* (2013.01)

(56) References Cited

U.S. PATENT DOCUMENTS

| | | | |
|---|---|---|---|
| 7,338,760 B2 * | 3/2008 | Gong et al. | 435/6.11 |
| 7,419,576 B1 | 9/2008 | Hata | |
| 8,168,442 B2 * | 5/2012 | Petersen et al. | 436/174 |
| 2006/0257290 A1 | 11/2006 | Shimizu | |
| 2010/0123457 A1 | 5/2010 | Shinoda | |
| 2010/0181199 A1 | 7/2010 | Sugiyama et al. | |

FOREIGN PATENT DOCUMENTS

| | | |
|---|---|---|
| JP | 2001-108619 A | 4/2001 |
| JP | 2005-30906 A | 2/2005 |
| JP | 2009-128152 A | 6/2009 |
| JP | 2009-222479 A | 10/2009 |
| JP | 2010-151777 A | 7/2010 |
| JP | 2010-216982 A | 9/2010 |
| WO | WO 03/025547 A1 | 3/2003 |
| WO | WO 2010/010858 A1 | 1/2010 |

OTHER PUBLICATIONS

Written Opinion of the International Searching Authority issued in PCT/JP2011/006933, dated Jan. 17, 2012.

Japanese Office Action dated Aug. 12, 2014, issued in corresponding Japanese Patent Application No. 2010-276376.

Extended European Search Report for EP 11846720.8, issued on Jun. 28, 2016.

* cited by examiner

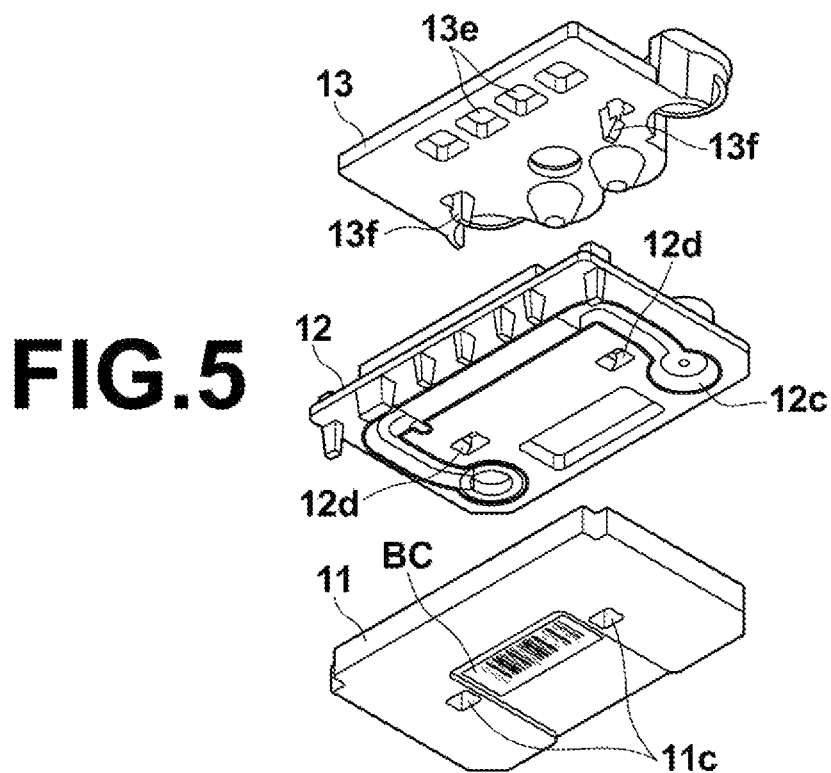
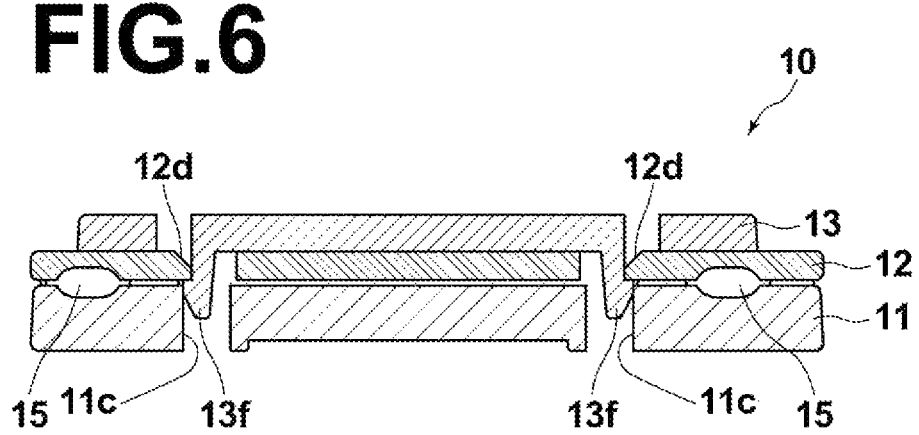

ASSAY CHIP

CROSS REFERENCE TO RELATED APPLICATIONS

This application is a Continuation of PCT International Application No. PCT/JP2011/006933 filed on Dec. 12, 2011, which claims priority under 35 U.S.C. §119(a) to Patent Application No. 2010-276376 filed in Japan on Dec. 10, 2010, all of which are hereby expressly incorporated by reference into the present application.

TECHNICAL FIELD

The present invention relates to an assay chip used in a light detection method for analyzing an analyte (substance to be examined) by detecting light output from a photoresponsive labeling substance that has bound to the analyte. Particularly, the present invention relates to an assay chip having both of a function for carrying out first reaction processing on an analyte in blood or the like, and a function for carrying out second reaction processing for detection.

BACKGROUND ART

Conventionally, plasmon sensors are known (please refer to U.S. Pat. No. 5,923,031 (Patent Document 1), for example). The plasmon sensors utilize the principle of surface plasmon resonance using evanescent waves, and perform quantitative assays on substances contained in samples. In Patent Document 1, an interface between a prism and a metal coating applied to a surface of the prism, and the metal coating being in contact with the sample, is illuminated with a light beam at a total reflection angle. Further, the reflection angle of the light beam that has been totally reflected at the interface is detected to perform a quantitative assay on a substance in the sample. Further, in Patent Document 1, a light source and a photo-detector (light detector) are movable to perform quantitative assays on plural samples stored in sample cells.

Further, fluorescence detection apparatuses utilizing the evanescent waves have been proposed (please refer to Japanese Unexamined Patent Publication No. 2009-128151 (Patent Document 2), for example). Patent Document 2 discloses a quantitative assay on an analyte by detecting fluorescence output when the analyte labeled with a fluorescent material or the like in a sample container is excited by evanescent waves.

Generally, when biochemical assay is performed by using the fluorescence detection apparatus as disclosed in Patent Document 2, it is necessary to carry out first reaction processing in advance before carrying out second reaction processing. In the first reaction processing, an analyte in a sample solution and a fluorescent label are bound together, and in the second reaction processing, the analyte labeled with the fluorescent material is captured by chemical bond.

Here, µTAS (Micro Total Analysis Systems), as disclosed in Japanese Unexamined Patent Publication No. 2009-222479 (Patent Document 3), may be adopted to reduce the amount of sample solution collected from a living body, and to increase a detection speed. At this time, desirable effects are achievable as for the second reaction processing. However, there are some problems as for the first reaction processing. Specifically, it is necessary that the analyte in the sample solution and the fluorescent label sufficiently bind to each other. However, it is difficult to sufficiently stir the solution in a fluidic channel of the µTAS to dissolve the fluorescent material in the solution. Consequently, the accuracy of detection of the analyte becomes lower.

As described above, a desirable method for the first reaction processing and a desirable method for the second reaction processing are different. Therefore, efficient measurement has been difficult by using conventional methods.

DISCLOSURE OF INVENTION

In view of the foregoing circumstances, it is an object of the present invention to provide an assay chip that can efficiently carry out first reaction through second reaction processing.

An assay chip according to the present invention is an assay chip used in a light detection method for analyzing an analyte by detecting light output from a photoresponsive labeling substance that has bound to the analyte, the assay chip comprising:

a pot for storing a sample solution and carrying out predetermined processing on the sample solution;

a fluidic channel having a detection region for detecting light output from the photoresponsive labeling substance, and through which the sample solution flows down;

an inlet for injecting the sample solution into the fluidic channel, and which is provided on the upstream side of the fluidic channel; and a suction opening for sucking, from the downstream side of the fluidic channel, the sample solution injected from the inlet, and which is provided on the downstream side of the fluidic channel.

Here, it is desirable that the detection region includes a dielectric plate for making excitation light for generating evanescent waves enter, and a metal coating applied to a predetermined region on a sample-solution-contact surface of the dielectric plate.

It is desirable that the pot includes a pot for pre-processing to carry out predetermined pre-processing on the sample solution, and/or a pot for first reaction processing to bind the analyte in the sample solution to the photoresponsive labeling substance.

Further, it is desirable that a predetermined dry reagent has been fixed onto an inner surface of at least one of the pot for pre-processing and the pot for first reaction processing. At this time, it is desirable that an uneven pattern is formed in a portion of the inner surface onto which the dry reagent is fixed to prevent detachment of the dry reagent therefrom.

Further, it is desirable that an opening of a pot onto the inner surface of which the dry reagent is fixed is sealed.

It is desirable that the inlet, the suction opening and the pot are linearly arranged.

It is desirable that the detection region is composed of a plurality of linearly-arranged detection sections.

An assay chip according to the present invention may include a fluidic channel member composed of a lower member and an upper member that form the fluidic channel therebetween, and at least a part of the fluidic channel member through which an optical path of light entering the detection region passes being light transmissive, and a cover member in which the pot is formed, and which is fitted with the fluidic channel member from the upper-member-side thereof.

It is desirable that a part of at least one of a lower surface of the lower member and an upper surface of the upper member, the part at which an ultrasonic horn for welding the lower member and the upper member together touches, is flat.

Further, it is desirable that an opening is provided in a region of the cover member facing the detection region.

A bar code representing predetermined information may be indicated on a surface of at least one of the fluidic channel member and the cover member.

Here, the "bar code" may be a one-dimensional bar code, or a two-dimensional bar code.

According to an assay chip of the present invention, the single assay chip includes a pot for storing a sample solution and carrying out predetermined processing on a sample solution, a fluidic channel having a detection region for detecting light output from a photoresponsive labeling substance, and through which the sample solution flows down, an inlet for injecting the sample solution into the fluidic channel, and which is provided on the upstream side of the fluidic channel, and a suction opening for sucking, from the downstream side of the fluidic channel, the sample solution injected from the inlet, and which is provided on the downstream side of the fluidic channel. Further, first reaction processing and the like are performed in the pot, and second reaction processing is performed in the fluidic channel. Therefore, the single assay chip can efficiently carry out first reaction through second reaction processing.

Here, when the detection region includes a dielectric plate for making excitation light for generating evanescent waves enter, and a metal coating applied to a predetermined region on a sample-solution-contact surface of the dielectric plate, the assay chip is usable in high-sensitivity measurement using evanescent waves.

When the pot includes a pot for pre-processing to carry out predetermined pre-processing on a sample solution and/or a pot for first reaction processing to bind a photoresponsive labeling substance to an analyte in the sample solution, appropriate processing is possible by using a specialized pot for each processing.

Here, when a predetermined dry reagent has been fixed onto an inner surface of at least one of the pot for pre-processing and the pot for first reaction processing, a user does not need to separately prepare a reagent for each processing. Therefore, efficient measurement is possible.

At this time, if an uneven pattern is formed in a portion of the inner surface onto which the dry reagent is fixed to prevent detachment of the dry reagent therefrom, it is possible to prevent detachment of the dry reagent during movement of the assay chip. Therefore, it is possible to prevent shift of the dry reagent from a predetermined position. Especially, when a sample solution is automatically dispensed into a pot to perform pre-processing or first reaction processing in a detection apparatus, stable processing is possible.

Further, when an opening of a pot onto the inner surface of which the dry reagent is fixed is sealed, it is possible to prevent moisture absorption, a change in quality or the like of the dry reagent.

If an inlet, a suction opening and a pot are linearly arranged, when first reaction processing through second reaction processing are automatically performed by moving a dispensing unit in a detection apparatus, it is sufficient if the dispensing unit is moved only linearly. Therefore, an automatic detection apparatus corresponding to an assay chip of the present invention is easily realizable.

Further, when there are plural detection regions (sections), if the plural detection regions are linearly arranged, an automatic detection apparatus corresponding to an assay chip of the present invention is easily realizable, because when a measurement unit is moved in a detection apparatus to automatically perform light detection processing, it is sufficient if the measurement unit is moved only linearly.

Further, when an assay chip of the present invention includes a fluidic channel member composed of a lower member and an upper member that form the fluidic channel therebetween, and at least a part of the fluidic channel member through which an optical path of light entering the detection region passes being transparent, and a cover member in which the pot is formed, and which is fitted with the fluidic channel member from the upper-member-side thereof, it is possible to simplify the shape of each member, and to obtain an excellent production characteristic. Therefore, it is possible to lower the production cost of the assay chip.

Further, when a part of at least one of a lower surface of the lower member and an upper surface of the upper member, the part at which an ultrasonic horn for welding the lower member and the upper member together touches, is flat, it is possible to improve the reliability of production when the lower member and the upper member are welded together by ultrasonic waves.

Further, when an opening is provided in a region of the cover member facing the detection region of the fluidic channel member so that detection of light is possible through the opening, a light detecting portion of the fluidic channel member is located at a lower position, by a distance corresponding to the thickness of the cover member in the vicinity of the opening, than the upper surface of the cover member. Therefore, the light detecting portion of the fluidic channel member is less likely to be touched by a user's hand directly. Hence, it is possible to prevent adhesion of a finger print.

Further, when a bar code representing predetermined information, such as an individual difference and a date of production of an assay chip, is indicated on a surface of at least one of the fluidic channel member and the cover member, it is possible to use the information to correct a measurement result obtained by using the assay chip. Specifically, it is possible to correct an error in the measurement result caused by an individual difference of the assay chip. Further, quality control or the like becomes possible. Hence, the product characteristic of the assay chip is improved.

BRIEF DESCRIPTION OF DRAWINGS

FIG. 5 is an exploded perspective view of the assay chip from the bottom thereof;

FIG. 6 is a cross-section of the assay chip at line VI-VI in FIG. 2;

BEST MODE FOR CARRYING OUT THE INVENTION

Figure 1:
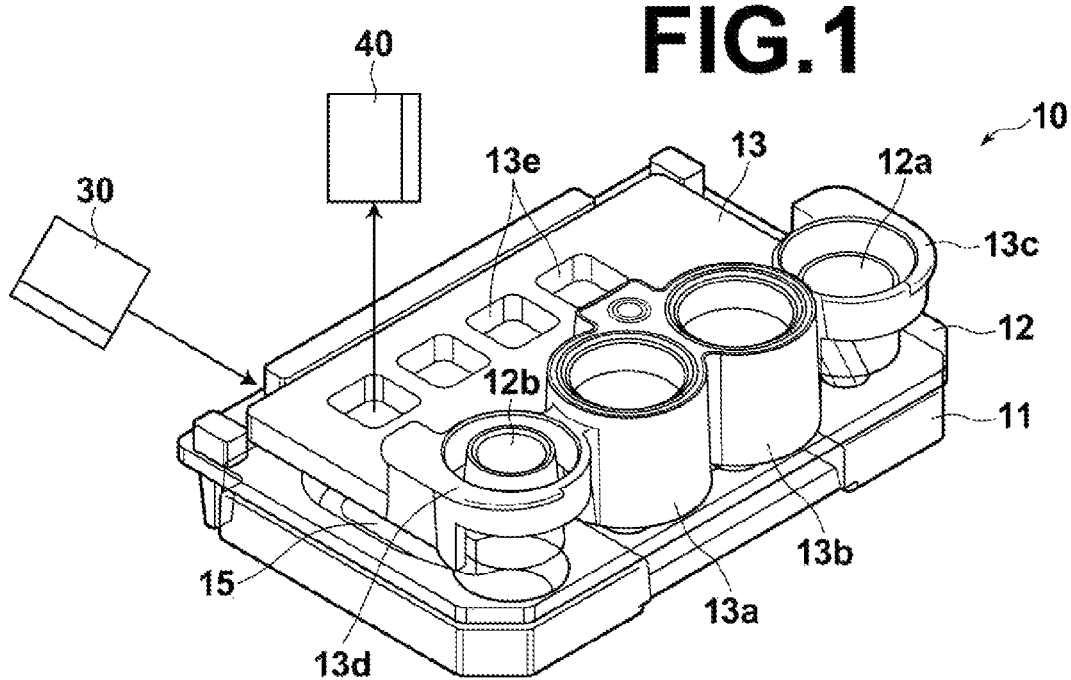
FIG. 1 is a perspective view illustrating a desirable embodiment of an assay chip of the present invention.
Figure 2:
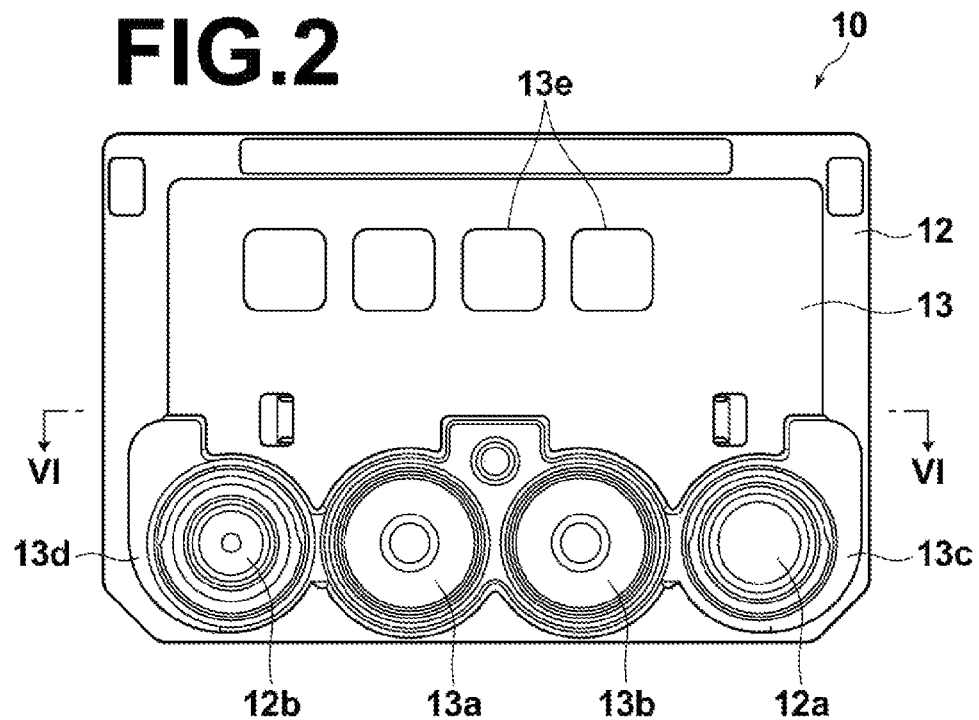
FIG. 2 is a top view of the assay chip.
Figure 3:
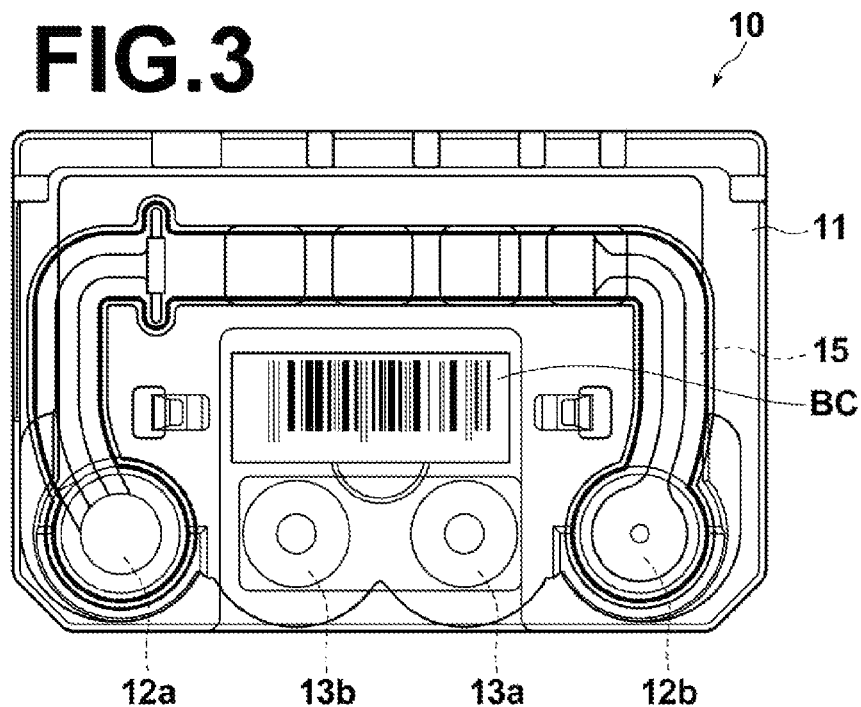
FIG. 3 is a bottom view of the assay chip.
Figure 4:
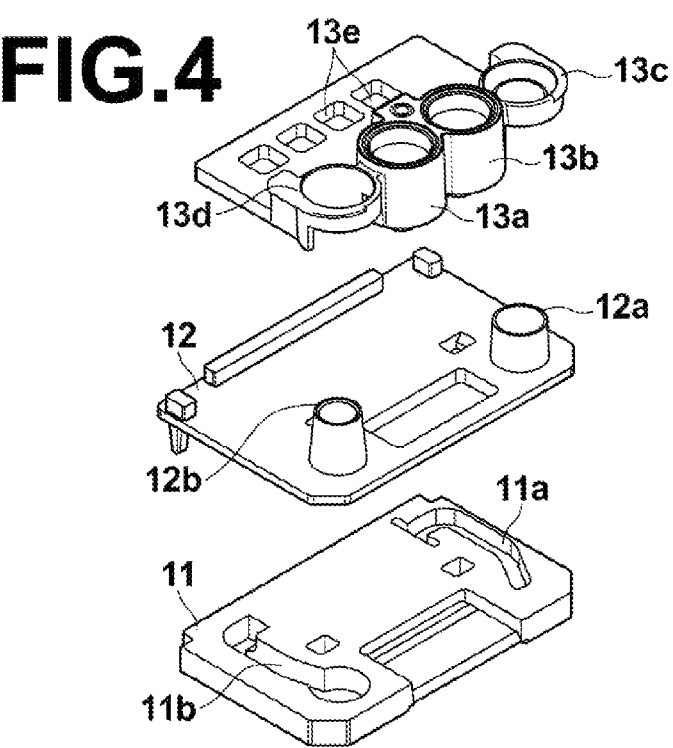
FIG. 4 is an exploded perspective view of the assay chip from the top thereof.
Figure 10:
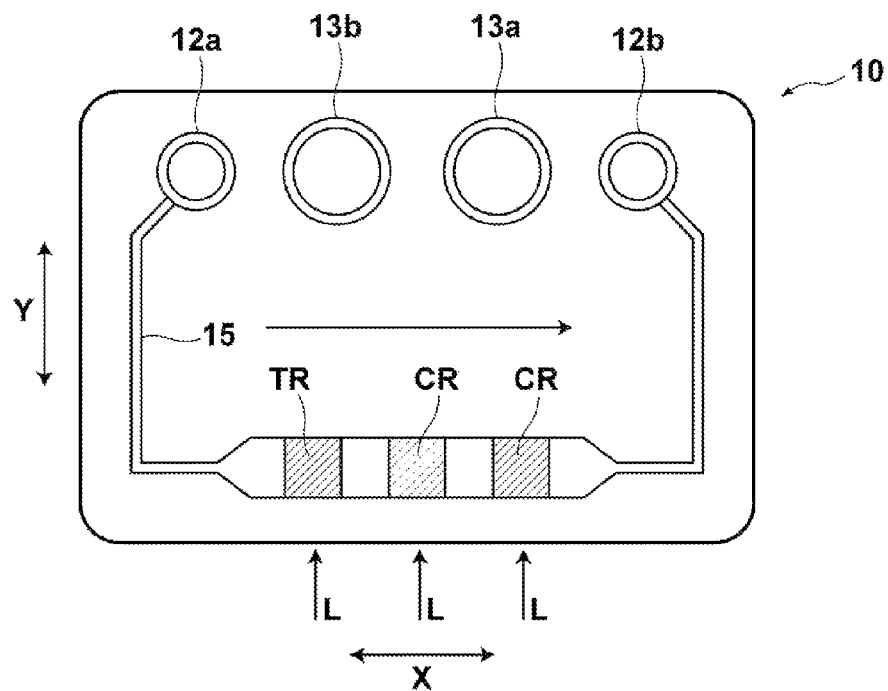
FIG. 10 is a schematic diagram illustrating the assay chip.

Hereinafter, embodiments of the present invention will be described in detail with reference to drawings. FIG. 1 is a perspective view illustrating a desirable embodiment of an assay chip according to the present invention. FIG. 2 is a top view of the assay chip, and FIG. 3 is a bottom view of the assay chip. FIG. 4 is an exploded perspective view of the assay chip from the top thereof, and FIG. 5 is an exploded perspective view of the assay chip from the bottom thereof. FIG. 6 is a cross-section of the assay chip at line VI-VI in FIG. 2. FIG. 10 is a schematic diagram illustrating the assay chip.

An assay chip 10 according to the present embodiment includes a fluidic channel member composed of a lower member 11 that transmits light and an upper member 12, and a cover member 13. A fluidic channel 15 is formed between the lower member 11 and the upper member 12, and the cover member 13 is fitted with the fluidic channel member from the upper-member-12 side of the fluidic channel member.

As illustrated in FIG. 4, groove portions 11a and 11b for forming the fluidic channel 15 are formed on an upper surface of the lower member 11. Further, as illustrated in FIG. 5, a groove portion 12c for forming the fluidic channel 15 is formed on a lower surface of the upper member 12. Accordingly, the fluidic channel 15 is formed between the lower member 11 and the upper member 12 when they are combined with each other.

The lower member 11 and the upper member 12 are made of dielectric material, such as transparent resin, and they are combined with each other by ultrasonic welding. As illustrated in FIGS. 4 and 5, a region of the lower surface of the lower member 11 and a region of the upper surface of the upper member 12, and the regions being located just above or just under the fluidic channel 15 are flat. Therefore, it is possible to make an ultrasonic horn for welding in close contact with the surfaces in these regions. Hence, it is possible to increase the reliability of ultrasonic welding. Especially, it is possible to prevent leakage of solution from the fluidic channel.

Further, an inlet 12a for injecting a sample solution into the fluidic channel 15 and a suction opening 12b for sucking, from the downstream side, the sample solution injected from the inlet 12a, both communicating with the fluidic channel 15, are formed on the upper surface of the upper member 12.

Further, a pot 13a for pre-processing that carries out predetermined pre-processing on the sample solution, a pot 13b for first reaction processing to bind a photoresponsive labeling substance to an analyte in the sample solution, an inlet insertion-hole 13c for inserting the inlet 12a, and a suction-opening insertion-hole 13d for inserting the suction opening 12b are formed on the upper surface of the cover member 13.

The pot 13a for pre-processing is a container for storing dry reagent for pre-processing, such as adjustment of pH of a sample so that the value of pH becomes appropriate for reaction at a downstream site. The pot 13b for first reaction processing is a container for storing fluorescent (second antibody) dry reagent that binds to the sample. Both of the pots 13a and 13b are independent containers that do not communicate with the fluidic channel 15.

Figure 12:
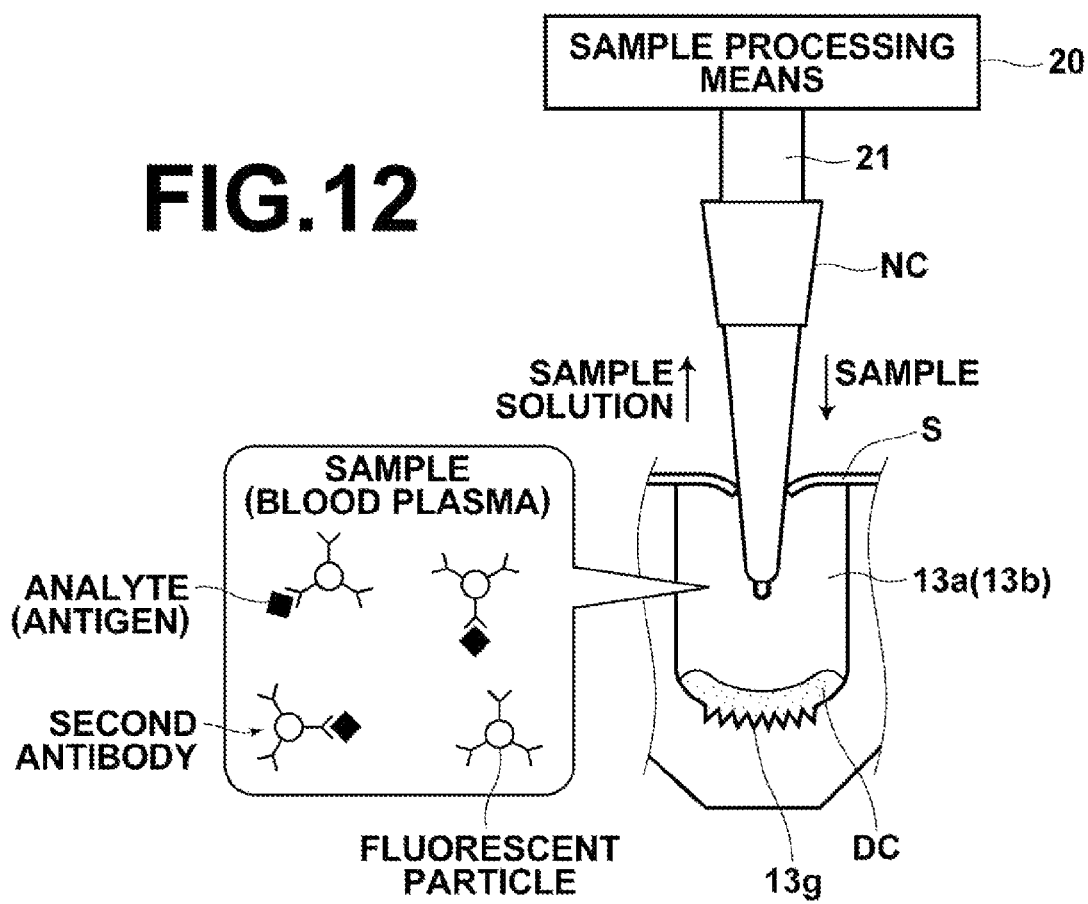
FIG. 12 is a schematic diagram illustrating a manner in which the sample processing means illustrated in FIG. 9 injects a sample present in the nozzle tip into a reagent cell, and stirs the sample.

As illustrated in FIG. 12, an uneven pattern 13g is formed in a portion onto which dry reagent DC is fixed to prevent detachment of the dry reagent DC therefrom. Therefore, it is possible to prevent detachment of the dry reagent DC during movement of the assay chip 10, or the like, and thereby preventing shift of the dry reagent DC from a predetermined position. Especially, when a sample solution is automatically dispensed into a pot to perform pre-processing or first reaction processing in a detection apparatus, stable processing is possible.

Further, an opening of the pot 13a for pre-processing and an opening of the pot 13b for first reaction processing are sealed by seal members S. When predetermined processing is performed on the sample, the seal members are perforated. Accordingly, it is possible to prevent moisture absorption, a change in quality of the reagent, or the like.

The pot 13a for pre-processing, the pot 13b for first reaction processing, the inlet insertion-hole 13c, and the suction-opening insertion-hole 13d are arranged close to each other and linearly. Therefore, when a dispensing unit is moved in the detection apparatus to automatically perform first reaction processing through second reaction processing, it is sufficient if the dispensing unit is moved linearly and only for a short distance. Hence, an automatic detection apparatus corresponding to the assay chip of the present invention is easily realizable. Further, the pot 13a for pre-processing, the pot 13b for first reaction processing, and the inlet 12a to the fluidic channel for second reaction processing (the inlet insertion-hole 13c) are arranged in this order. Therefore, when each processing step advances to the next step, it is sufficient if the dispensing unit is moved only in one direction. Hence, extremely efficient measurement is possible.

In the present embodiment, two pots, namely the pot 13a for pre-processing and the pot 13b for first reaction processing are provided. However, it is not necessary that the two pots are provided. For example, the pot 13a for pre-processing is not provided, and pre-processing may be performed at a different place other than the assay chip 10.

As schematically illustrated in FIG. 10, the inlet 12a communicates with the suction opening 12b through the fluidic channel 15. When negative pressure is applied from the suction opening 12b, a sample (test sample, specimen or the like) is injected into the fluidic channel 15 from the inlet 12a, and flows in the fluidic channel 15. Further, the sample is discharged from the suction opening 12b.

Further, test region TR for detecting an analyte in the sample and control regions CR are formed in the fluidic channel 15. The control regions CR are formed on the downstream side of the test region TR. A first antibody is fixed in the test region TR, and a labeled antibody is captured by using a so-called sandwich method. Further, a reference antibody is fixed in the control regions CR. When the sample solution flows on the control regions CR, the reference antibody in the control regions CR captures the fluorescent material. Two control regions CR, namely, so-called negative-type control region CR and so-called positive-type control region CR are formed. The negative-type control region detects non-specific adsorption, and the positive-type control region detects a difference in reactivity depending on an individual difference between samples. The test region TR and the two control regions CR function as a second reaction region.

The test region TR and the two control regions CR are linearly arranged. Therefore, when a measurement unit is moved in a detection apparatus to automatically perform light detection processing, it is sufficient if the measurement unit is moved only linearly. Hence, an automatic detection apparatus corresponding to an assay chip of the present invention is easily realizable.

Further, the fluidic channel 15 is substantially U-shaped, and composed of a detection region portion, an introduction portion, and a discharge portion. The detection region portion includes test region TR and two control regions CR, and is linearly shaped. The introduction portion connects the upstream end of the detection region portion to an inlet 12a. The discharge portion connects the downstream end of the detection region portion to a suction opening 12b. Further, a pot 13a for pre-processing and a pot 13b for first reaction processing are arranged between the inlet 12a and the suction opening 12b. The direction of arrangement of the pot 13a for pre-processing, the pot 13b for first reaction processing, the inlet insertion-hole 13c, and the suction-opening insertion-hole 13d, and the linear detection region portion are parallel to each other. Such an arrangement of the assay chip 10 can minimize the size of the assay chip 10.

As illustrated in FIG. 1, four openings 13e are formed in a region of the cover member 13, the region being located just above the detection region. Three of the four openings 13e correspond to the test region TR and the two control regions CR. One more opening 13e is provided on the downstream side of the three openings 13e.

The opening 13e located on the most-downstream side is provided to detect, based on transmission of light emitted from an LED (light-emitting diode), whether a leading end of the sample solution has reached the position. For example, light emitted from the LED (hereinafter, also referred to as LED light) illuminates the assay chip 10 from the down side thereof toward the upper side thereof, and the light amount of the LED light is detected at an upper position. At this time, if the sample solution has not reached the position of the most-downstream side opening 13e, a part of LED light (approximately 4%) is reflected at each of a boundary between the lower member 11 constituting the fluidic channel member and the fluidic channel 15 and a boundary between the fluidic channel 15 and the upper member 12. Therefore, in total, the light amount drops by approximately 8%. In contrast, if the sample solution has reached the most-downstream side opening 13e, the refractive index of the sample solution and the refractive index of transparent resin are close to each other, and the LED light is not substantially reflected at the boundaries. Therefore, the light amount does not substantially drop. Hence, the detected amount of LED light is higher by approximately 8% when the sample solution has reached the most-downstream side opening 13e, compared with a case in which the sample solution has not reached the most-downstream side opening 13e. In this manner, it is possible to detect, based on a change in the amount of detected LED light, whether the leading end of the sample solution has reached the most-downstream side opening 13e (in other words, whether the sample solution has passed through the entire detection region portion).

When the openings 13e corresponding to the test region TR, the two control regions CR and the LED light detection unit are provided as described above, the light detecting portion of the fluidic channel member is located at a lower position, by a distance corresponding to the thickness of the cover member 13 in the vicinity of the openings 13e, than the upper surface of the cover member 13. Therefore, the light detecting portion in the fluidic channel member is less likely to be touched by a user's hand directly. Hence, it is possible to prevent adhesion of a finger print to the fluidic channel member.

As illustrated in FIG. 6, two hook pins 13f are formed on the lower surface of the cover member 13. Further, hook portions 12d are formed in the upper member 12 of the fluidic channel member. The hook pins 13f are inserted into the hook portions 12d, and hooked on edges of the hook portions 12d. Further, insertion holes 11c for inserting the hook pins 13f into the lower member 11 are formed in the lower member 11. Since the assay chip 10 is structured in such a manner, it is possible to produce the assay chip 10 by producing the fluidic channel member by welding the lower member 11 and the upper member 12 together, and later by simply fitting the cover member 13 with the fluidic channel member. Therefore, it is possible to simplify the shape of each member, and an excellent production characteristic is obtainable. Hence, it is possible to reduce the production cost.

The fluidic channel member and the cover member 13 are separate members. Therefore, it is possible to produce each of the reagent fixed onto the inside of the fluidic channel 15 in the fluidic channel member and the reagents fixed onto the inside of the pot 13a for pre-processing and the inside of the pot 13b for first reaction processing in the cover member 13 in circumstances under different conditions, such as the length of dry time and temperature. Hence, it is possible to optimize the circumstances of producing each reagent.

Further, bar code BC may be indicated on a surface of the assay chip 10, such as a lower surface of the lower member 11, for example. The bar code BC may represent predetermined information, such as an individual difference and a date of production of the assay chip 10. In such an embodiment of the present invention, it is possible to use the information to correct a measurement result obtained by using the assay chip 10. Specifically, it is possible to correct an error in the measurement result caused by an individual difference of the assay chip. Further, quality control or the like becomes possible. Hence, the product characteristic of the assay chip is improved.

Figure 7:
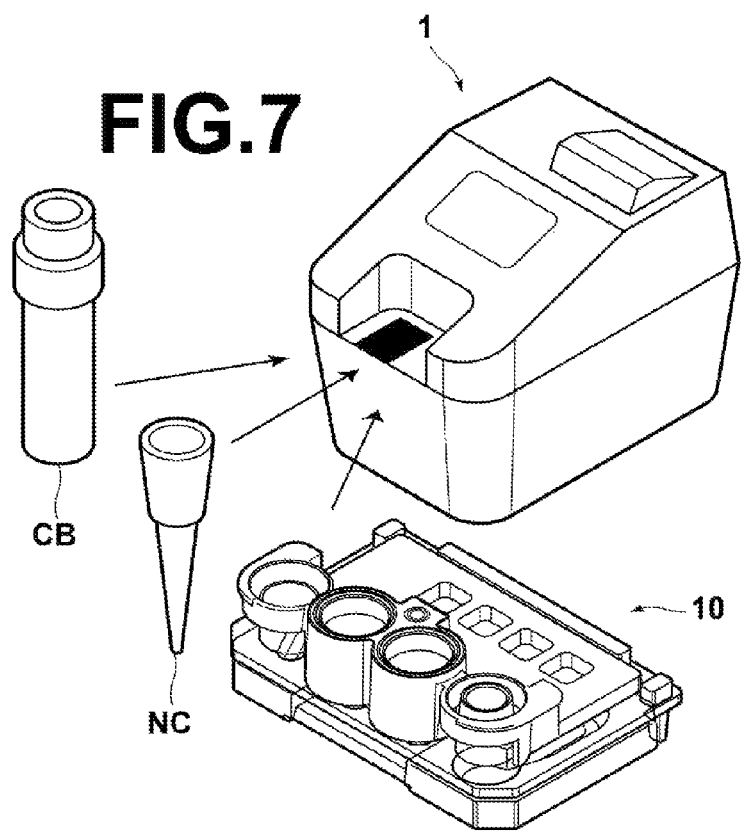
FIG. 7 is a schematic diagram illustrating a fluorescence detection apparatus using the assay chip.
Figure 8:
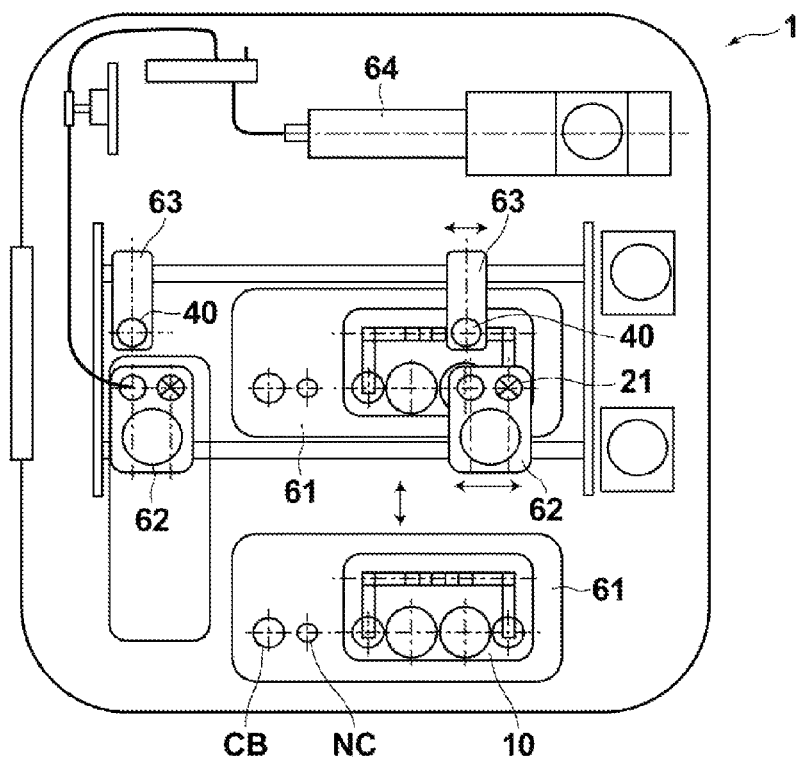
FIG. 8 is a schematic diagram illustrating the structure of a measurement unit of the fluorescence detection apparatus.
Figure 9:
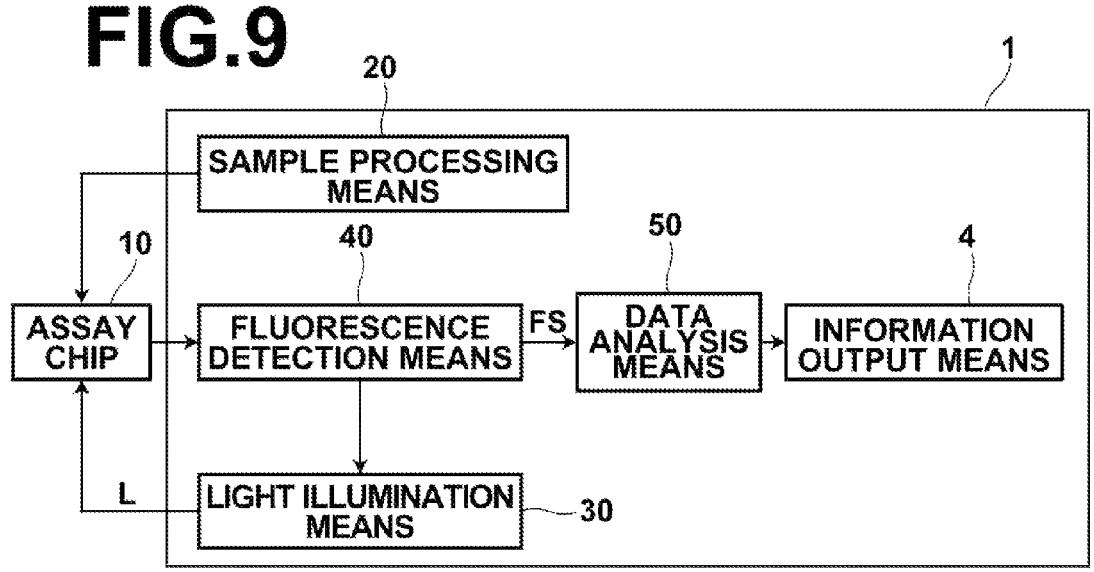
FIG. 9 is a block diagram of the fluorescence detection apparatus.
Figure 11:
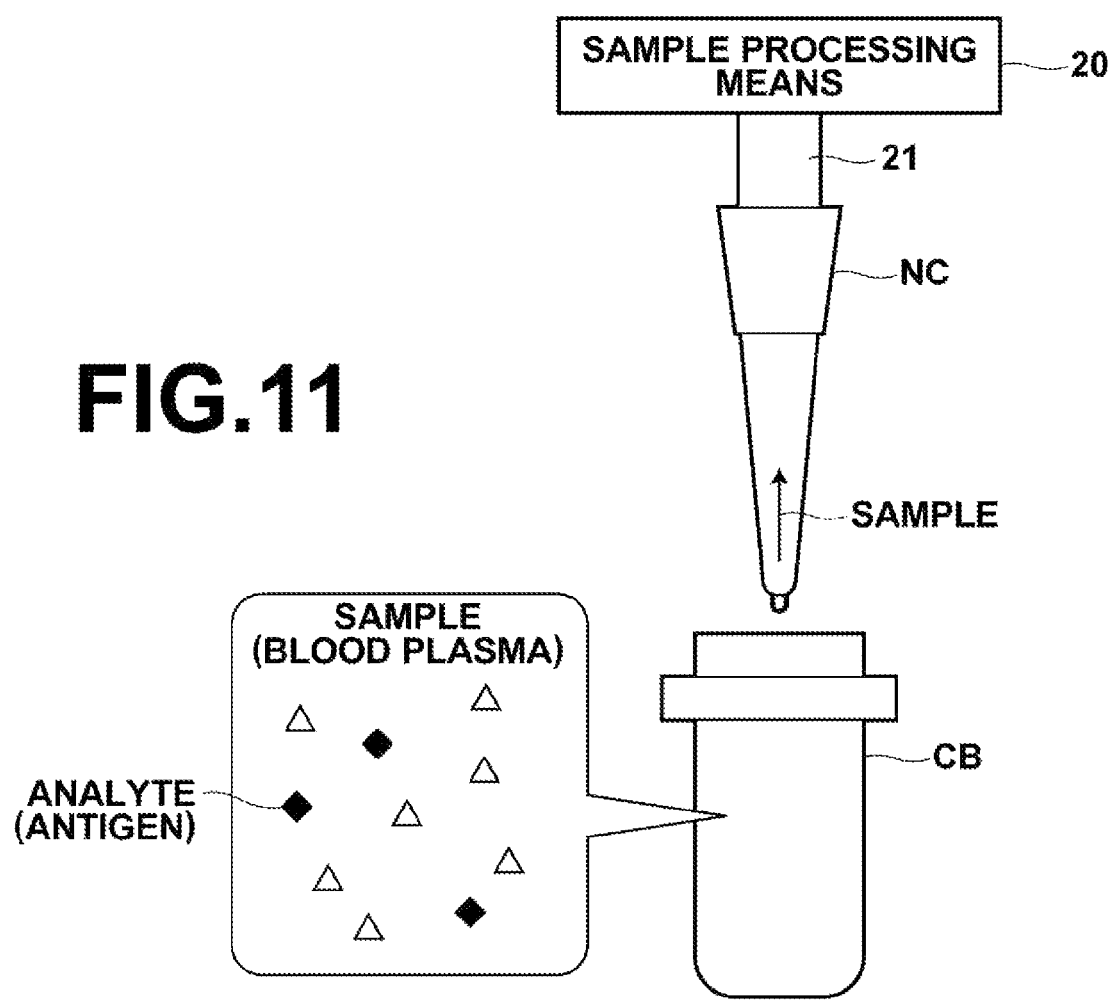
FIG. 11 is a schematic diagram illustrating a manner in which a sample processing means illustrated in FIG. 9 extracts a sample from a sample container by using a nozzle tip.
Figure 13:
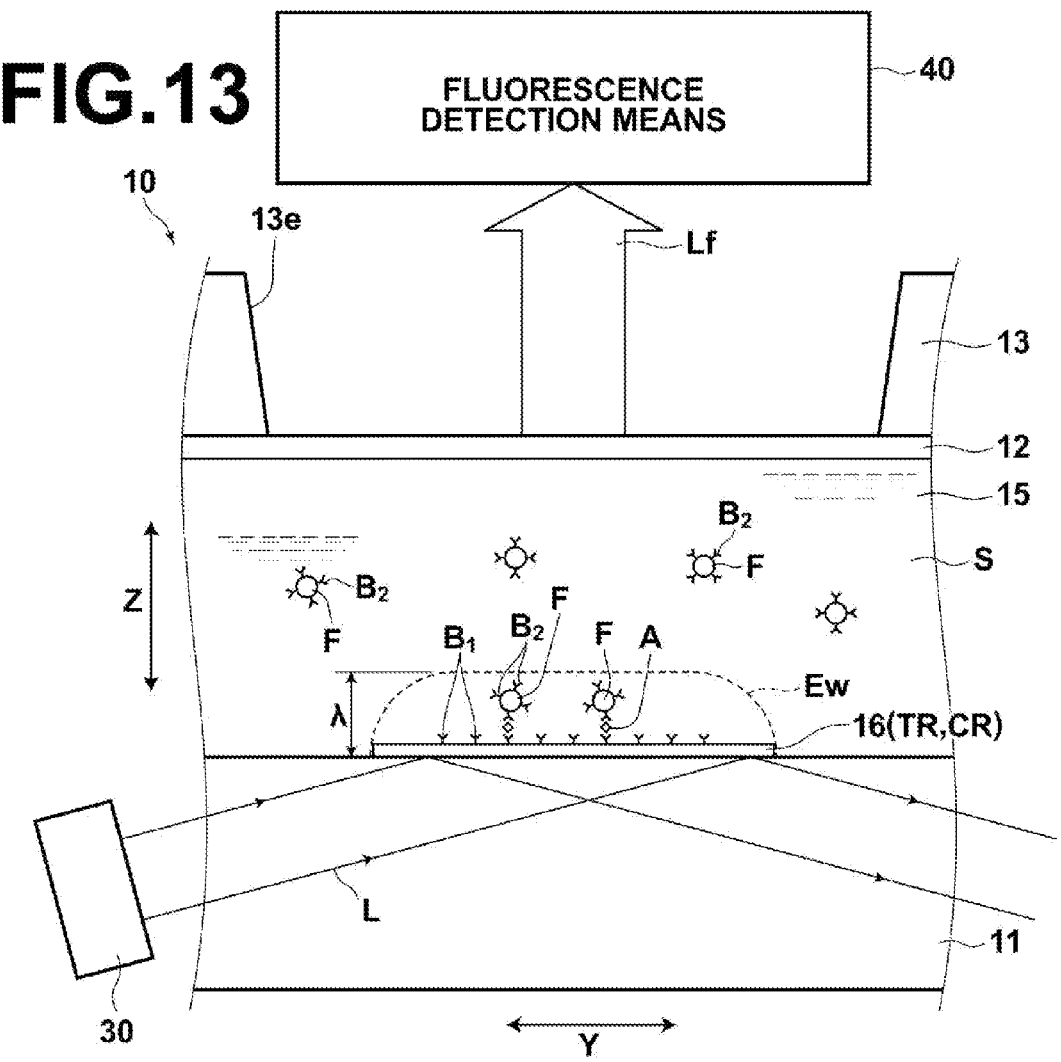
FIG. 13 is a schematic diagram illustrating an example of a light illumination means and a fluorescence detection means illustrated in FIG. 9.
Figure 14:
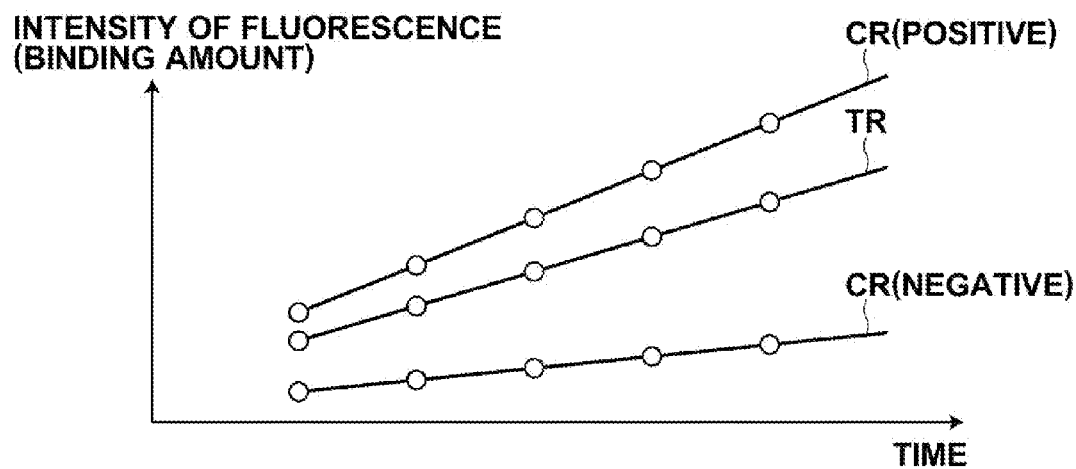
FIG. 14 is a graph illustrating a manner in which a data analysis means illustrated in FIG. 9 performs quantitative or qualitative analysis by using a rate method.

Next, a fluorescence detection apparatus using the assay ship 10 according to an embodiment of the present invention will be described. FIG. 7 is a schematic diagram illustrating an example of a fluorescence detection apparatus using the assay chip. FIG. 8 is a schematic diagram illustrating the structure of a measurement unit of the fluorescence detection apparatus. FIG. 9 is a block diagram of the fluorescence detection apparatus. FIG. 10 is a schematic diagram illustrating the assay chip. FIG. 11 is a schematic diagram illustrating a manner in which a sample processing means illustrated in FIG. 9 extracts a sample from a sample container by using a nozzle tip. FIG. 12 is a schematic diagram illustrating a manner in which the sample processing means illustrated in FIG. 9 injects a sample present in the nozzle tip into a reagent cell, and stirs the sample. FIG. 13 is a schematic diagram illustrating an example of a light illumination means and a fluorescence detection means illustrated in FIG. 9. FIG. 14 is a graph illustrating a manner in which a data analysis means illustrated in FIG. 9 performs quantitative or qualitative analysis by using a rate method.

A fluorescence detection apparatus 1 is, for example, an immune assay apparatus using surface plasmon resonance.

As illustrated in FIGS. 7 and 8, when the fluorescence detection apparatus 1 carries out assay, sample container CB in which a sample is stored, nozzle tip NC that is used to extract the sample and a reagent, and the assay chip 10 are loaded on a table 61. All of the sample container CB, the nozzle tip NC, the assay chip 10 and the table 61 are disposable members, which will be discarded after single use. The fluorescence detection apparatus 1 carries out quantitative or qualitative assay on an analyte in a sample, while making the sample flow in a micro fluidic array 15 in the assay ship 10.

The fluorescence detection apparatus 1 includes a sample processing means 20, a light illumination means 30, a fluorescence detection means 40, a data analysis means 50, and the like. The sample processing means 20 extracts, by using nozzle tip NC, a sample from sample container CB in which the sample is stored. Further, the sample processing means 20 produces a sample solution by stirring the extracted sample to mix the sample with a reagent.

As illustrated in FIG. 8, the table 61 on which the sample container CB, the nozzle tip NC and the assay chip 10 have been loaded is moved from a loading position to a predetermined measurement position. At the measurement position, a dispensing unit 62 on which the sample processing means 20 has been loaded and a measurement unit 63 on which the light illumination means 30 and the fluorescence detection means 40 have been loaded move with the assay chip 10 therebetween. Each of the dispensing unit 62 and the measurement unit 63 moves parallel to the direction of arrangement of the pot 13a for pre-processing, the pot 13b for first reaction processing, the inlet insertion-hole 13c, and the suction-opening insertion-hole 13d. The apparatus is structured in such a manner that predetermined processes as described below can be automatically carried out.

When start of assay is instructed, the sample processing means 20 sucks a sample from sample container CB by using nozzle tip NC, as illustrated in FIG. 11. Then, the sample processing means 20 perforates seal member S of the pot 13a for pre-processing, as illustrated in FIG. 12, and repeats injection of the sample into the pot 13a for pre-processing and suction of the sample therefrom. Accordingly, reagent DC in the pot 13a for pre-processing and the sample are sufficiently mixed together and stirred. After then, the sample processing means 20 sucks the sample solution by using the nozzle tip NC again. This operation is carried out similarly also with respect to the pot 13b for first reaction processing. Then, a sample solution in which the surface of an analyte (antigen) A present in the sample is labeled with second antibody B2 contained in the reagent is produced. The second antibody B2 is a second binding substance that specifically binds to the analyte A. After the sample processing means 20 sets the nozzle tip NC in which the sample solution is stored on the inlet 12a, negative pressure is applied to the suction opening 12b to cause the sample solution in the nozzle tip NC to flow into the fluidic channel 15 for second reaction processing.

FIG. 13 is a schematic diagram illustrating an example of the light illumination means 30 and the fluorescence detection means 40. Descriptions with reference to FIG. 13 will focus on test region TR. However, control regions CR are illuminated with excitation light L in a similar manner. The light illumination means 30 in FIG. 9 illuminates the lower member 11 (dielectric plate) and a metal coating 16 of the test region TR, from a side of the fluidic channel member (lower member 11) of the assay chip 10, with excitation light L. The excitation light L is output in such a manner to enter the lower member 11 and the metal coating 16 in the test region TR at an incident angle that achieves total reflection conditions. The fluorescence detection means 40 is composed of a photodiode, a COD, a CMOS or the like, for example. The fluorescence detection means 40 detects, as fluorescent signal FS, fluorescence Lf generated in the test region TR by illumination with excitation light L by the light illumination means 30.

When the excitation light L illuminated by the light illumination means 30 enters an interface between the lower member 11 (dielectric plate) and the metal coating 16 at a specific incident angle greater than or equal to a total reflection angle, evanescent waves Ew penetrate into sample S on the metal coating 16. Further, surface plasmon is excited in the metal coating 16 by the evanescent waves Ew. Then, a distribution of electric fields is induced on the surface of the metal coating 16, and an electric field enhanced region is generated. Then, the fluorescent label substance F that has bound is excited by the evanescent waves Ew, and generates enhanced fluorescence.

The data analysis means 50 illustrated in FIG. 9 analyzes an analyte based on a time-series change of fluorescence signal FS detected by the fluorescence detection means 40. Specifically, the intensity of fluorescence changes based on the amount of fluorescent label substance F that has bound. Therefore, the intensity of fluorescence changes as time passes, as illustrated in FIG. 14. The data analysis means 50 obtains plural fluorescent signals FS in a predetermined time period (for example, five minutes) at predetermined sampling intervals (for example, five second cycle). Further, the data analysis means 50 analyzes the rate of change in the intensity of fluorescence according to time. Accordingly, the data analysis means 50 performs quantitative analysis on the analyte in the sample (rate method). The analysis result is output from an information output means 4, such as a monitor or a printer.

So far, desirable embodiments of the present invention have been described. It is needless to say that various improvements and modifications are possible without departing from the gist of the present invention.

What is claimed is:

1. An assay chip used in a light detection method for analyzing an analyte by detecting light output from a photoresponsive labeling substance that has bound to the analyte, the assay chip comprising:
   a pot for storing a sample solution and carrying out predetermined processing on the sample solution;
   a fluidic channel having a detection region for detecting light output from the photoresponsive labeling substance, and through which the sample solution flows down;
   an inlet for injecting the sample solution into the fluidic channel, and which is provided on the upstream side of the fluidic channel; and
   a suction opening for sucking, from the downstream side of the fluidic channel, the sample solution injected from the inlet, and which is provided on the downstream side of the fluidic channel;
   wherein at least a first reaction processing pot, which stores a photoresponsive labeling substance and performs a primary reaction process that binds the photoresponsive labeling substance and the analyte, is provided as the pot, and
   wherein the suction opening, the first reaction processing pot, and the inlet are provided on a one dimensional straight line in this order.

2. An assay chip, as defined in claim 1, wherein the detection region includes a dielectric plate for making excitation light for generating evanescent waves enter, and a metal coating applied to a predetermined region on a sample-solution-contact surface of the dielectric plate.

3. An assay chip, as defined in claim 1, wherein the pot further includes a pot for pre-processing, to carry out pre-determined pre-processing on the sample solution, wherein said pot for pre-processing is separate from the first reaction processing pot.

4. An assay chip, as defined in claim 3, wherein a predetermined dry reagent has been fixed onto an inner surface of the pot for pre-processing.

5. An assay chip, as defined in claim 1, wherein a predetermined dry reagent has been fixed onto an inner surface of the pot for first reaction processing.

6. An assay chip, as defined in claim 4, wherein an uneven pattern is formed in a portion of the inner surface onto which the dry reagent is fixed to prevent detachment of the dry reagent therefrom.

7. An assay chip, as defined in claim 5, wherein an uneven pattern is formed in a portion of the inner surface onto which the dry reagent is fixed to prevent detachment of the dry reagent therefrom.

8. An assay chip, as defined in claim 4, wherein an opening of the pot for pre-processing is sealed.

9. An assay chip, as defined in claim 5, wherein an opening of the pot for first reaction processing is sealed.

10. An assay chip, as defined in claim 1, wherein the detection region is composed of a plurality of linearly-arranged detection sections.

11. An assay chip, as defined in claim 1, the assay chip further comprising:
a fluidic channel member including a lower member and an upper member that form the fluidic channel therebetween, and at least a part of the fluidic channel member through which an optical path of light entering the detection region passes being light transmissive; and
a cover member in which the pot is formed, and which is fitted with the fluidic channel member from the upper-member-side thereof.

12. An assay chip, as defined in claim 1, wherein a part of at least one of a lower surface of the lower member and an upper surface of the upper member, the part at which an ultrasonic horn for welding the lower member and the upper member together touches, is flat.

13. An assay chip, as defined in claim 1, wherein an opening is provided in a region of the cover member facing the detection region.

14. An assay chip, as defined in claim 1, wherein a bar code representing predetermined information is indicated on a surface of at least one of the fluidic channel member and the cover member.

15. An assay chip as defined in claim 1, wherein:
a plurality of linear detection regions are provided parallel to a line from the suction opening to the inlet that passes through the first reaction processing pot as parallel rows.

16. An assay chip as defined in claim 1, further comprising:
a preliminary processing pot for performing preliminary processing prior to a first reaction process.

17. An assay chip as defined in claim 16, wherein:
the suction opening, the preliminary processing pot, the first reaction processing pot, and the inlet are provided linearly in this order.

18. An assay chip as defined in claim 17, wherein:
a plurality of linear detection regions are provided parallel to a line from the suction opening to the inlet that passes through the preliminary processing pot and the first reaction processing pot as parallel rows.

* * * * *